(12) United States Patent
Kawasaki

(10) Patent No.: US 9,706,796 B2
(45) Date of Patent: Jul. 18, 2017

(54) HANDS FREE PUMPING BUSTIER

(71) Applicant: MEDELA HOLDING AG, Baar (CH)

(72) Inventor: Don Kawasaki, Toronto (CA)

(73) Assignee: MEDELA HOLDING AG, Baar (CH)

( * ) Notice: Subject to any disclaimer, the term of this patent is extended or adjusted under 35 U.S.C. 154(b) by 0 days.

(21) Appl. No.: 15/235,412

(22) Filed: Aug. 12, 2016

(65) Prior Publication Data

US 2017/0042256 A1    Feb. 16, 2017

Related U.S. Application Data

(60) Provisional application No. 62/204,096, filed on Aug. 12, 2015.

(51) Int. Cl.
| | |
|---|---|
| *A41C 3/00* | (2006.01) |
| *A41C 3/04* | (2006.01) |
| *A61M 1/06* | (2006.01) |
| *A41C 5/00* | (2006.01) |
| *A41C 3/02* | (2006.01) |

(52) U.S. Cl.
CPC .............. *A41C 3/04* (2013.01); *A41C 5/00* (2013.01); *A61M 1/062* (2014.02); *A41C 3/02* (2013.01); *A61M 2209/088* (2013.01)

(58) Field of Classification Search
CPC .......... A41C 3/00; A41C 3/007; A41C 3/0014
USPC ................. 450/36, 54, 57, 58, 74; 2/104
See application file for complete search history.

(56) References Cited

U.S. PATENT DOCUMENTS

| | | | |
|---|---|---|---|
| 4,667,345 A * | 5/1987 | Jachowski | ............. A41D 15/00 2/91 |
| 5,575,768 A | 11/1996 | Lockridge et al. | |
| 6,004,186 A | 12/1999 | Penny | |
| 6,178,784 B1 * | 1/2001 | Marley, Jr. | ........... A41C 3/0014 450/92 |
| 6,213,840 B1 | 4/2001 | Han | |
| 6,227,936 B1 | 5/2001 | Mendoza | |
| 6,440,100 B1 | 8/2002 | Prentiss | |
| 6,645,041 B2 | 11/2003 | Sarensen | |
| 6,866,558 B2 | 3/2005 | Luciano et al. | |

(Continued)

OTHER PUBLICATIONS

International Search Report and Written Opinion, International Application No. PCT/CA2016/050953, mailed Oct. 26, 2016.

*Primary Examiner* — Gloria Hale
(74) *Attorney, Agent, or Firm* — Marshall, Gerstein & Borun LLP

(57) ABSTRACT

A hands free pumping bustier provides a nursing woman with a convenient way of supporting funnel-shaped breast shields that are used as the nipple and breast interface during expression of milk. The bustier features breast shield ports having additional support members that extend upward to a top band of the bustier, providing superior support for the breast shields, enabling the bustier to accommodate differently sized breast shields, and simplifying manufacture of the bustier. The bustier further features a hook at the top of the zipper, which helps the nursing woman to easily maintain the garment around her body as she uses both hands to secure and zip the zipper. The bustier is made of a stretch nylon multi-filament yarn, such that it has adequate stretch capability to accommodate women of different body sizes and shapes while maintaining comfortable compression of the breast shields against their bodies.

20 Claims, 8 Drawing Sheets

(56) References Cited

U.S. PATENT DOCUMENTS

| | | | |
|---|---|---|---|
| 6,887,217 B1 | 5/2005 | Logan | |
| 6,974,361 B2 | 12/2005 | Cravaack et al. | |
| 7,028,509 B2 * | 4/2006 | Mitchell | A41C 3/0014 66/176 |
| 7,051,557 B2 * | 5/2006 | Mitchell | A41C 3/0014 450/92 |
| 7,094,217 B2 | 8/2006 | Fialkoff | |
| 7,430,883 B2 | 10/2008 | Sorensen | |
| 7,549,302 B2 | 6/2009 | Duckham et al. | |
| 7,654,115 B2 * | 2/2010 | Duckham | A41C 3/0014 66/176 |
| 7,662,019 B2 * | 2/2010 | Faircloth | A41C 3/0014 2/243.1 |
| 8,057,452 B2 | 11/2011 | Fialkoff | |
| 8,137,153 B2 * | 3/2012 | Bell | A61M 1/06 450/36 |
| 8,192,247 B2 | 6/2012 | Abbaszadeh | |
| 8,323,070 B2 | 12/2012 | Abbaszadeh | |
| 8,414,353 B1 | 4/2013 | Leavell | |
| 8,469,770 B2 | 6/2013 | Alva | |
| 8,523,629 B2 | 9/2013 | Pundyk | |
| 2007/0161330 A1 | 7/2007 | Whitehead et al. | |
| 2011/0314587 A1 | 12/2011 | Ritchie | |
| 2013/0122780 A1 | 5/2013 | McCall | |
| 2015/0133028 A1 | 5/2015 | Applewhite | |

* cited by examiner

HANDS FREE PUMPING BUSTIER

CROSS-REFERENCE TO RELATED APPLICATION

This application claims priority to U.S. Provisional Patent Application No. 62/204,096 filed Aug. 12, 2015 entitled "Hands Free Pumping Bustier," the entire disclosure of which is hereby incorporated by reference.

FIELD OF THE DISCLOSURE

This disclosure relates generally to a bustier for a nursing woman using a breast pump to extract milk from her breasts for storage and subsequent feeding of an infant. The bustier supports the portion of a breast pump system known as a breast shield, freeing the nursing woman's hands to carry out other tasks besides holding one or two breast shields in place.

BACKGROUND

Breastfeeding of an infant provides numerous benefits to the infant and the breastfeeding woman. Breastmilk contains all of the nutrients a baby needs in the exact amounts required for optimal growth and development. Breastfed babies are healthier, having fewer middle ear infections, fewer respiratory infections, a decreased risk of developing allergies, cancer, childhood diabetes, and obesity, and being less prone to develop heart diseases, eczema, and asthma. For the breastfeeding woman, breastfeeding reduces post-delivery bleeding and chances of anaemia, aids in the uterus returning to its original size after birth, and burns up to an extra 500 calories per day.

However, not every nursing woman is able to breastfeed an infant on demand due to work schedules and other time demands. Accordingly, many nursing women use a breast pump to extract and store milk for feeding an infant. Breast pump systems routinely include a breast shield, which is a funnel-like apparatus having a conical region that is placed against the breast with the nipple in the center of the breast shield. Upon the application of negative pressure, the nipple is drawn toward, and often into, a tubular portion of the breast shield known as the nipple tunnel. The nipple tunnel of the breast shield is connected to other components of a breastmilk collection kit. This connection permits application of intermittent (i.e., cyclical) negative pressure to the interior of the breast shield, and also provides a flow path for breastmilk expressed into the nipple tunnel to be collected in a collection receptacle. The collection receptacle may be a breastmilk container having a threaded cap that can serve as a bottle for feeding an infant. A nursing woman generally has to hold the breast shield against her breast manually in order to pump milk.

Predictably, holding the breast shield in place is inconvenient and limits the tasks that the woman could otherwise accomplish while pumping. Although various brassieres and bustiers have been developed to hold the breast shield in place, such brassieres and bustiers have generally failed to adequately secure the breast shield and have required holding or frequent adjusting of the breast shield.

SUMMARY

A hands free pumping bustier is hereby disclosed. The hands free pumping bustier is a generally tubular bustier that stretches around a wearer's body, covering the wearer's breasts except the nipples and securing a breast shield adjacent to each breast. The tubular bustier has two bands, a top band and a bottom band that help to secure the bustier in place. The bottom band may be an integrated bottom band that is knit into the bustier through the manufacturing process in a manner that does not require an exposed seam along its bottom. The unitary construction of an integrated bottom band simplifies the manufacturing process by eliminating the need to sew a separate bottom band into the bustier while enhancing the comfort of the bustier by eliminating a seam that would otherwise exist along the bottom of the bustier. The bottom band also helps hold the bustier against the rib cage area of the wearer. The top band can be formed of a suitable, stretchable material, such as a wide strip of elastic, can be connected to the material to form the rest of the bustier. The top band further ensures that the bustier does not slip down as the weight in one or more collection receptacles increase during a pumping session. The portion of the bustier intended to be worn on the back of the wearer, or back portion, can be formed of a single ply of material, which reduces the weight of the hands free pumping bustier.

The portion of the bustier intended to cover the breasts and breast shields of the wearer, or front portions, can be formed of a double ply of material. The front portions provide additional support for the breast shield when inserted and for the breasts when worn. In other words, a bustier constructed in accordance with the principles of the present disclosure includes a tubular knit device having multilayer portions in the construction. In an embodiment, the combination of a single ply material back portion and double ply material front portions forms layers that improve the ability of the bustier, or garment, to adapt to different body types, and specifically to differences in chest and breast sizes.

To this end, the bustier can be formed to provide front portions of increased elastic modulus as compared to a back portion of the bustier, both to better support the breastmilk collection apparatus inserted therethrough and to avoid the breastmilk collection apparatus slipping downwardly away from the breast as either collection receptacles of the breastmilk collection apparatus fill with breastmilk, without relying on compressive forces to support one or two collection receptacles in place as the collection receptacles fill with breastmilk. The bustier is also formed to provide the back portion with a decreased elastic modulus as compared to the front portions. In an embodiment, the reduced elastic modulus of the back portion is achieved by providing a single ply area that allows the front portions to extend out only where needed by breast tissue.

Unlike known knitted tubular fabrics of a single layer, such as SANTONI®, and known paneling techniques of non-tubular materials sewn together to create a fit, a bustier constructed in accordance with the principles of the present disclosure combines two seemingly contradictory techniques to produce a bustier that fits small ribcage measurements and large breasts without unduly compressing the breasts. Thus, the two concepts of stretch and custom fit are combined to form a single bustier that meets the needs of a wide variety of users, while addressing the enlarged condition of a mother's lactating breasts as compared to her ribcage size.

The bustier can be formed of a tubular knit material manufactured, for example, on a circular knitting machine. Alternately, the bustier may be manufactured on a flat knitting machine or on a Warp knitting machine. The bustier can have a generally tubular body that is split axially in order to allow a wearer to wrap the bustier around her body. The bustier has a first side and a second side along the axial split. A strip of material comprising a first set of zipper teeth is attached to the first side, and a strip of material comprising a second set of zipper teeth mateable to the first set of zipper teeth is attached to the second side. A slider to mate the first set of zipper teeth and second set of zipper teeth is located on either the first set of zipper teeth or the second set of zipper teeth. A protective strip of material is also sewn to either the first side or second side of the bustier on the interior side of the bustier, underneath a strip of material comprising zipper teeth. The protective strip of material is of sufficient width that, when the hands free pumping bustier is zipped, the protective strip extends underneath the both strips of material on which zipper teeth are located. The protective strip thus protects the skin of the wearer from being accidentally caught between the sets of zipper teeth when the zipper is being closed and also protects the skin of the wearer from the roughness of the zipper or strips of material on which the zipper teeth are located.

A hook or other suitable fastening device can be located at the top of the bustier next to the top band with the hook fixed on one of the first and second sides and the loop secured to the other of the first and second sides. Prior to being zipped shut, the tops of the first and second sides of the bustier can be secured to one another in a suitable manner, such as by inserting the hook into the complementary loop. The hook makes it easier to put on the hands free pumping bustier because, instead of needing to hold the first and second sides of the bustier together with one hand while zipping with the other hand, the wearer can use both hands to zip the bustier shut.

Further, a bustier constructed in accordance with the principles of the present disclosure increases in tension in the region of the fastening device when the bustier is stretched to be worn by a user. As a result, the increasing tension in the region of the fastening device, which must also accommodate multiple breast and rib cage sizes, can render the device difficult to apply for use. As a result, a suitable fastening device, such as a hook, button, snap, plastic closure or any other suitable closure device, can be incorporated into the top band at or near the first and second sides in order to pre-secure and simplify the application of the bustier to the wearer and ease the connection of the first and second sides, despite the tension arising during application of the bustier. When connected, the fastening device works in conjunction with the top band to distribute the tensile forces across the top band more uniformly. In an embodiment, a hook is selected as the fastening device due to the ease of connecting the hook while the tension of the top band increases during application of the bustier.

In an embodiment, a first end portion of the hook, which may, by way of example only, be a generally S-shaped or "6"-shaped metallic or plastic hook, can be attached to the top band on the first side of the bustier underneath the strip of material comprising the first set of zipper teeth, and a second end portion of the hook is exposed and may be received in the complementary loop on the second side of the bustier underneath the strip of material comprising the second set of zipper teeth. When the hands free pumping bustier is zipped closed, the protective strip is located underneath both the hook and loop, thus protecting the skin of the wearer from contact with the hook.

The bustier constructed in accordance with the principles herein can include two apertures, or breast shield ports, to accommodate the nipple tunnels of the breast shields, which are located adjacent to the breasts of the wearer when placed in the proper position for pumping breastmilk. Construction of a breast shield port involves providing solutions to a number of problems, for example providing sufficient tension across the breasts to support the full collection receptacles and breast shield. Simply increasing the tension of the bustier overall not only renders the garment more difficult to apply, but can also interfere with milk flow and/or cause discomfort to wearers with particularly large breasts.

In order to avoid the disadvantages arising from merely increasing the overall tension of the bustier, additional support in the breast shield port area can be achieved by constructing a bustier in accordance with the principles herein. To this end, a suitable additional support member in the breast shield port area can be joined to the top band in a suitable fashion. For example, the additional support member can be formed using a continuous piece of elastic joined to the top band in a suitable manner.

The continuous piece of elastic can be sewn to the top band, or secured to the top band in any other suitable fashion such as via an attachment device, weaving, or any other suitable method or device for attaching the continuous piece of elastic to the top band. By selecting a suitable additional support member, such as a continuous piece of material that can transmit force for the additional support of the breast shield port area, the force can be transferred along the elastic to the top band. Further, the additional support member can reinforce cut fabric areas in the region of ports formed in the bustier.

From a manufacturing perspective, the continuous piece of elastic can be sewn on a straight line instead of sewing a circle or other more complex shape. As a result, the task of ensuring that all fabric edges are caught in the seam while a controllable, uniform tension is provided by the additional support member can be achieved. The resulting uniform tension of the additional support member can ensure that good adherence to the tolerances required for the breast shield port to accommodate a number of different breast shield sizes can be achieved, while simultaneously providing enough tension to ensure that increasing collection receptacle weight during a pumping session can be counteracted by the connection of the additional support members to the top band. The additional support member can form a drop-shaped "drops of life" opening about the port. The additional support member may have a stacked or side-by-side configuration between the port and the top band.

The process of creating a slit that can be opened to facilitate applying elastic to the straight edge of the slit is much easier to manufacture than applying elastic to a curved edge. The additional support member can be formed of one or more pieces of material, such as elastic, and need not be continuous so long as suitable tension can be achieved with the additional support member. Alternatively, a keyhole-shaped piece of fabric can be provided in the region of the breast shield port and extend to the top band.

In an embodiment, the edge of each breast shield port is surrounded by elastic, and the elastic extends superiorly of the breast shield port, up to the top band of the bustier. The elastic surrounding each breast shield port provides several benefits, four of which are listed below.

First, the elastic transmits most of the downward force exerted on the breast shield ports by the breast shields and pumping apparatus up to the top band of the bustier. Because the top band is secured at a narrower part of the body above the midline of the breasts and is formed of elastic itself, the top band does not easily slide downward. Thus, the connection of the elastic surrounding the breast shield ports to the top band helps to prevent the bustier and breast shields from sliding downward. Second, the fabric material surrounding the breast shield ports is susceptible to unraveling without a finished edge. The elastic provides a finished edge to prevent such unraveling. Third, having elastic surround the end of each breast shield port makes it possible for the hands free pumping bustier to secure multiple breast shield sizes because the elastic can stretch to accommodate the nipple tunnel of various sized breast shields. Fourth, the manufacturing of the breast shield port is simplified by this design because a slit can be cut downward from the portion of the material forming the bustier just below the top band and a sewing machine can be used to join the top portion of the slit and finish the breast shield port, which is not the case in bustiers for breast pumps where a hole is unconnected to the top band.

With the exception of the top band, the hands free pumping bustier is preferably made from a circular knitted fabric tube comprising stretch nylon multi-filament yarn. Ideally, the fabric from which the hands free pumping bustier is made is stiff enough to provide women of different body sizes and shapes with the proper support for breast shields, but is flexible enough to avoid excessive compression of the breasts that could result in discomfort or harm to a woman's milk supply. Further, the material must have strong recovery characteristics to ensure that the breast shields are secure against the body during the entire pumping process, even as the size of the breasts decreases as milk is removed. To achieve these ends, the fabric of the hands free pumping bustier ideally has a low modulus of elasticity at each position to which it might be stretched. In some embodiments, the fabric of the hands free pumping bustier may, for example, be a SANTONI® knit.

A bustier constructed in accordance with the principles herein can facilitate hands-free breastpumping. In an embodiment, the bustier includes a top band, a bottom band, a main body intermediate the top band and the bottom band, a first side, a second side, and a pair of breast shield ports each having an additional support member such as an elastic edges, the additional support members of the breast shield ports extending superiorly of the breast shield ports to the top band. The exemplary bustier may further comprise a hook connected to the top band of the bustier, a first set of zipper teeth connected to a first side of the bustier and a second set of zipper teeth mateable to the first set of zipper teeth and connected to a second side of the bustier, a slider located either on the first set of zipper teeth or on the second set of zipper teeth, and/or a protective liner.

The exemplary bustier may further comprise a back portion having a single ply of material, front portions having two ply of material, a hook including a hooking portion, a loop portion into which the hooking portion can be inserted, and/or a main body made from a stretch nylon multi-filament yarn. In an exemplary bustier of the present disclosure, the bottom band and the main body may be knit together and the top band may be made from an elastic material that differs from material used to make the main body.

Also disclosed herein is a method of putting on a bustier to facilitate hands-free breastpumping, comprising placing breast shields against a wearer's breasts, wrapping a main body of a bustier around the wearer's body, ensuring that nipple tunnels of the breast shields extend through breast shield ports of the main body of the bustier; and securing a first side of the main body to a second side of the main body. The method may further include inserting a hooking portion of a hook into a loop portion, mating a first set of zipper teeth with a second set of zipper teeth, ensuring that a protective strip is properly aligned, and/or attaching the remainder of a breast pump apparatus to the nipple tunnels of the breast shield.

Also disclosed herein is a method of manufacturing a bustier to facilitate hands-free breastpumping, comprising using a circular, flat, or Warp knitting machine to produce an outer ply tubular knit piece of material having a first knitting pattern, a second knitting pattern, a transition line between the first and second knitting patterns, and a bottom band knit into the outer ply tubular knit piece of material along the transition line, cutting or casting off the tubular knit piece of material circumferentially at the first knitting pattern to create a top and circumferentially at the second knitting pattern to create a bottom and axially in one location to create a first side and a second side, creating inner ply front portions using a circular, flat, or Warp knitting machine, sewing the inner ply front portions to the outer ply tubular knit piece of material to create a main body and two-ply front portions, creating breast shield ports by cutting a slit downward from the top of the main body into each two-ply front portion, sewing elastic around each slit, and sewing the upper portion of each slit shut, and stitching an elastic band to the top to make a top band. The method may also include attaching a protective liner, attaching a first set of zipper teeth and a second set of zipper teeth that is mateable to the first set of zipper teeth, and/or attaching a hook portion and loop to the top band.

DETAILED DESCRIPTION OF THE DRAWINGS

Figure 1:
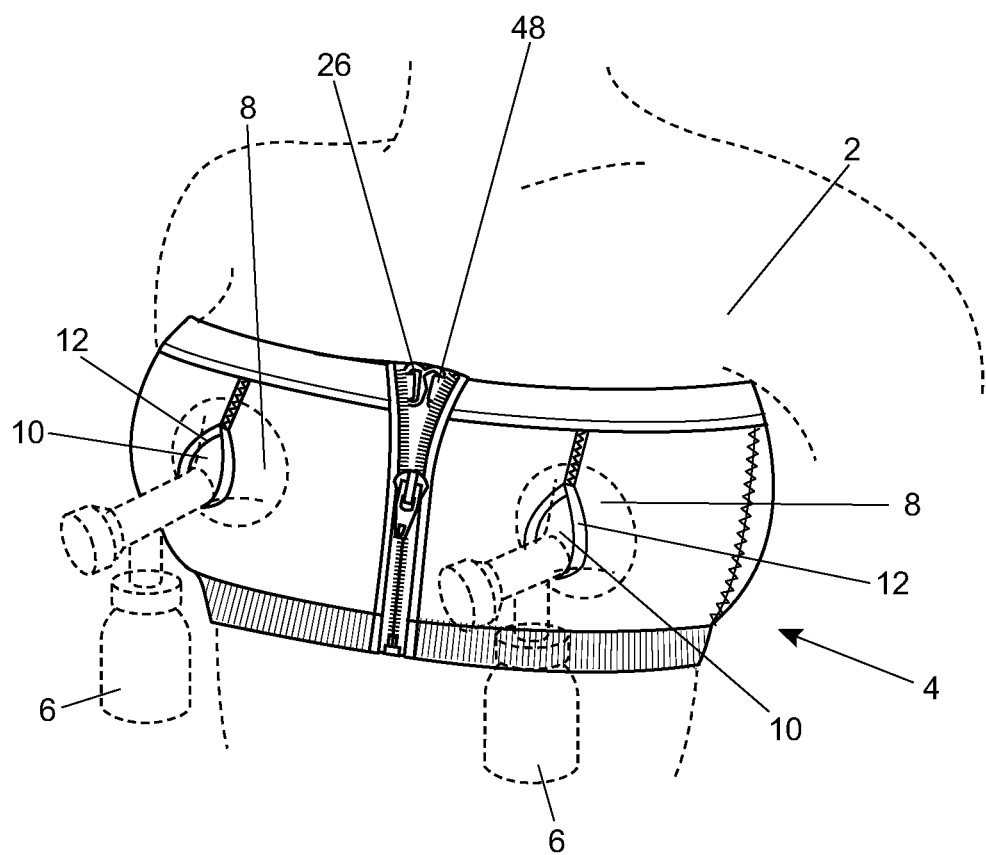
FIG. 1 is a perspective view of a hands free pumping bustier on a wearer with the pumping apparatus shown in dotted lines.

FIG. 1 illustrates a wearer 2 wearing a hands free pumping bustier 4. Breastmilk collection apparatuses 6, including breast shields 8, are secured to the wearer 2 by the hands free pumping bustier 4. The breast shields 8 are located inside the hands free pumping bustier 4 next to the breasts of the wearer 2. The nipple tunnels 10 of the breast shields 8 extend through breast shield ports 12 of the hands free pumping bustier 4 and are then connected to breastmilk collection and negative pressure source components of the breastmilk collection apparatuses 6 outside the hands free pumping bustier 4.

Figure 2:
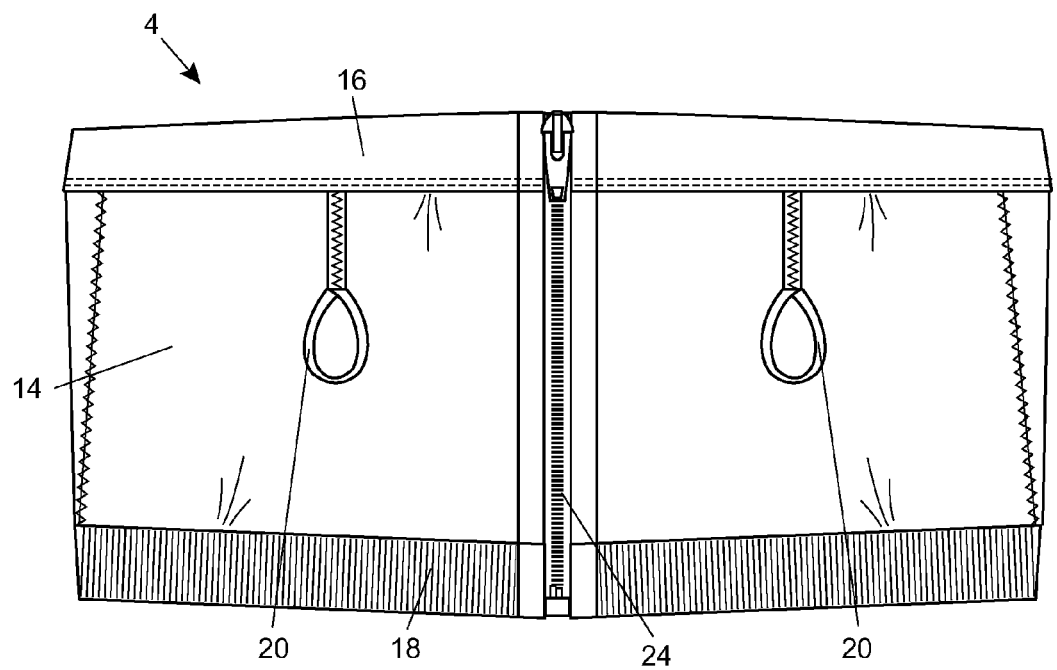
FIG. 2 is a front view of a hands free pumping bustier in a closed position having each additional support member in a stacked configuration.
Figure 3:
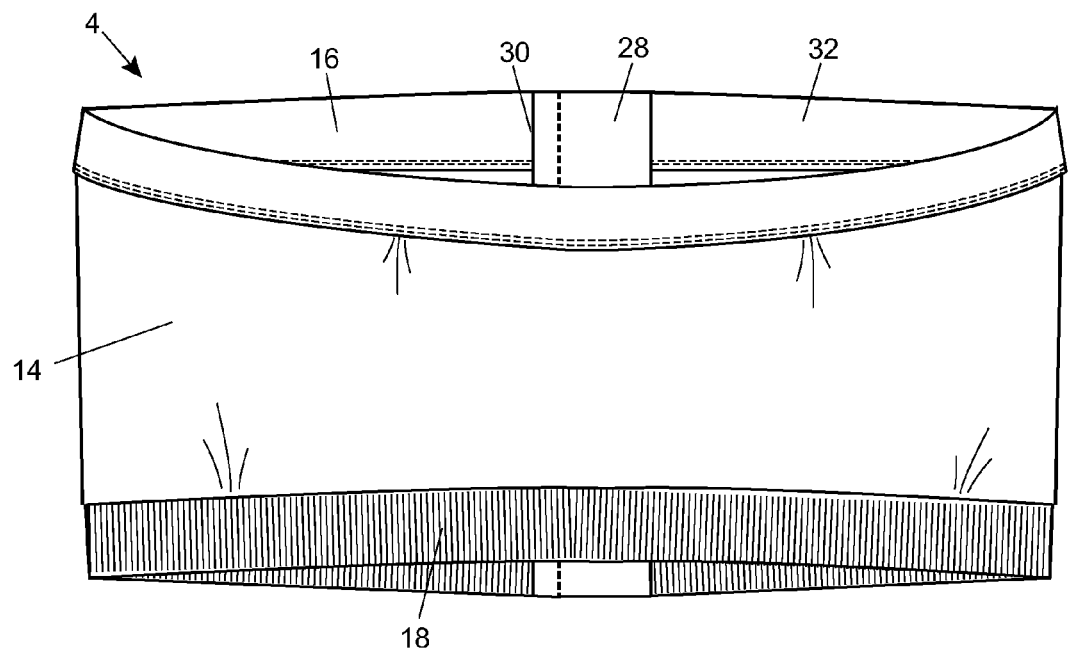
FIG. 3 is a rear view of a hands free pumping bustier in a closed position having each additional support member in a stacked configuration.

FIGS. 2 and 3 depict a front view and rear view, respectively, of the hands free pumping bustier 4 in a closed, zipped position. The hands free pumping bustier 4 has a main body 14 that is attached at its top to a top band 16 and is formed integrally at its bottom with a bottom band 18. The top band 16 is a separate elastic material sewn to the main body 14. The top band 16 is less elastic than the main body 14. The bottom band 18 is knit into the main body 14 during the manufacturing process and does not have a seam along its bottom, which reduces the amount of sewing necessary to create the hands free pumping bustier 4 and enhances comfort for the wearer 2 by eliminating a seam that would otherwise exist.

Figure 11:
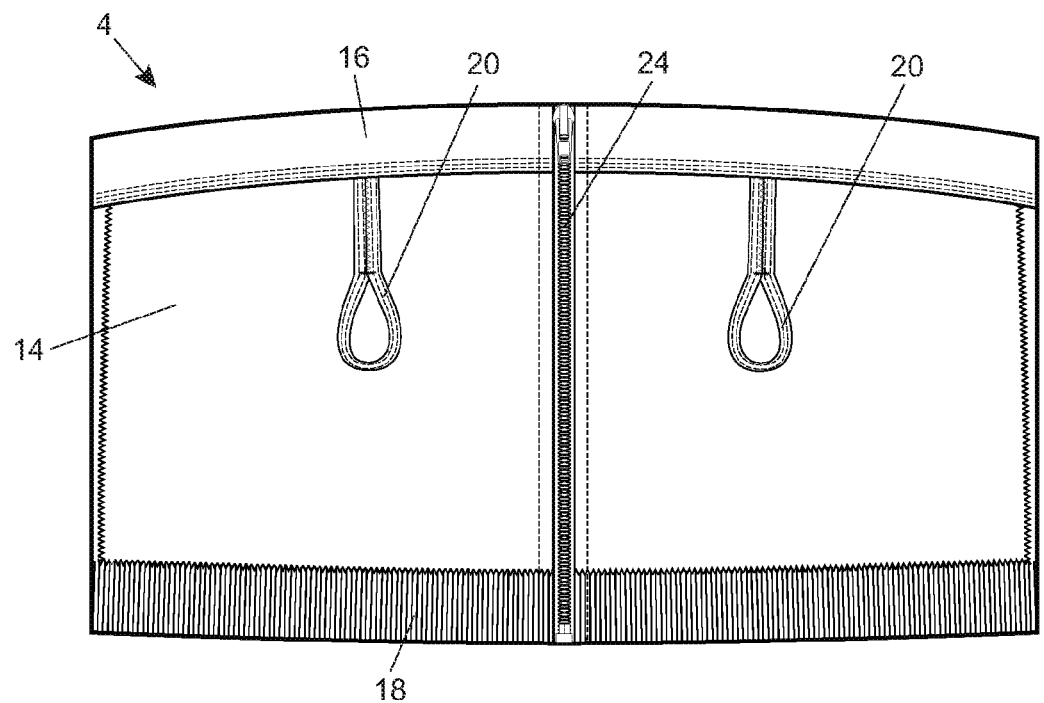
FIG. 11 is a front view of a hands free pumping bustier in a closed position having each additional support member in a side-by-side configuration.

As shown in FIG. 2, the breast shield ports 12 have additional support members 20, which may be elastic edges. The additional support members 20 of the breast shield ports 12 extend vertically upward (i.e., superiorly) from the breast shield ports 12 all the way up to the top band 16. During manufacturing, prior to the top band 16 being attached, slits that will become breast shield ports 12 can be cut downward from the portion of the main body 14 to which the top band 16 will eventually be attached. As used herein, slits refers to the cut material that will form the breast shield ports 12, while the breast shield ports 12 refer to the finalized apertures in the main body 14 of the hand free pumping bustier 4. The additional support members 20 can be sewn in along the edges of the slits, and the top portions of the slits that are lined with the additional support members 20 can be sewn together to finalize the breast shield ports 12. The additional support members 20 may be sewn together in a stacked configuration in which one portion of the additional support member 20 overlaps another portion of the additional support member 20 between the breast shield port 12 and the top band 16, as shown in FIG. 2. Alternately, the additional support members 20 may be sewn together in a side-by-side configuration in which one portion of the additional support member 20 is next to another portion of the additional support member 20 between the breast shield port 12 and the top band 16, as shown in FIG. 11. This manufacturing process is simpler than manufacturing processes in which a hole must be cut in material without any cut being made to an edge of the material. Further, when a breast shield 8 is inserted through a breast shield port 12, the weight of the breastmilk collection apparatus 6 can cause a downward force to be exerted on the breast shield port 12. The additional support members 20 of the breast shield port 12 transmit this downward force up to the elastic top band 16. The anatomy of the wearer 2, as shown in FIG. 1, results in the top band 16 being better able to resist the downward force than any other portion of the hands free pumping bustier 4 because the top band 16 is located at a narrow portion of the body of the wearer 2 above the wider portion of the body where the breast shield port 12, breast shield 8, and breastmilk collection apparatus 6 is located. Moreover, the elastic of the top band 16 is stiffer and less stretchy than the material of the main body 14 and is thus less likely to deform in response to a downward force. Thus, the transmission of the downward force up the additional support members 20 to the elastic top band 16 provides optimal securement of the hands free pumping bustier 4 and breast shield 8. In addition, the additional support members 20 prevent the material forming the cylindrical tube 14 from unraveling at the breast shield ports 12, and the additional support members 20 accommodate breast shields 8 having differently sized nipple tunnels 10.

As shown in FIGS. 1 and 2, the main body 14 along with the top band 16 and bottom band 18 is closed by a zipper 24, and a hook 26, such as a generally S-shaped or "6"-shaped hook, is attached to the top band 16 interior to the zipper 24. A wearer 2 may insert the hook 26 into a complementary loop 48 prior to zipping the zipper 24 in order to maintain the hand free pumping bustier 4 around the body as the wearer uses both hands to secure and zip the zipper 24. In other embodiments within the scope of the present disclosure, the hook 26 may be any other type of fastening device such as a clasp, catch, snap, latch, buckle or other known mechanism for holding a first side 30 and a second side 32 of the hands free pumping bustier 4 together. As illustrated in FIG. 3, a protective strip of material 28 is attached to either the first side 30 or the second side 32 of the hands free pumping bustier 4 interior of both the zipper 24 and the hook 26. The protective strip 28 prevents the skin of the wearer 2 from being caught in the zipper 24 as the two sides of the zipper are zipped, and further protects the skin of the wearer 2 from being chafed by the zipper 24 or the hook 26.

Figure 4:
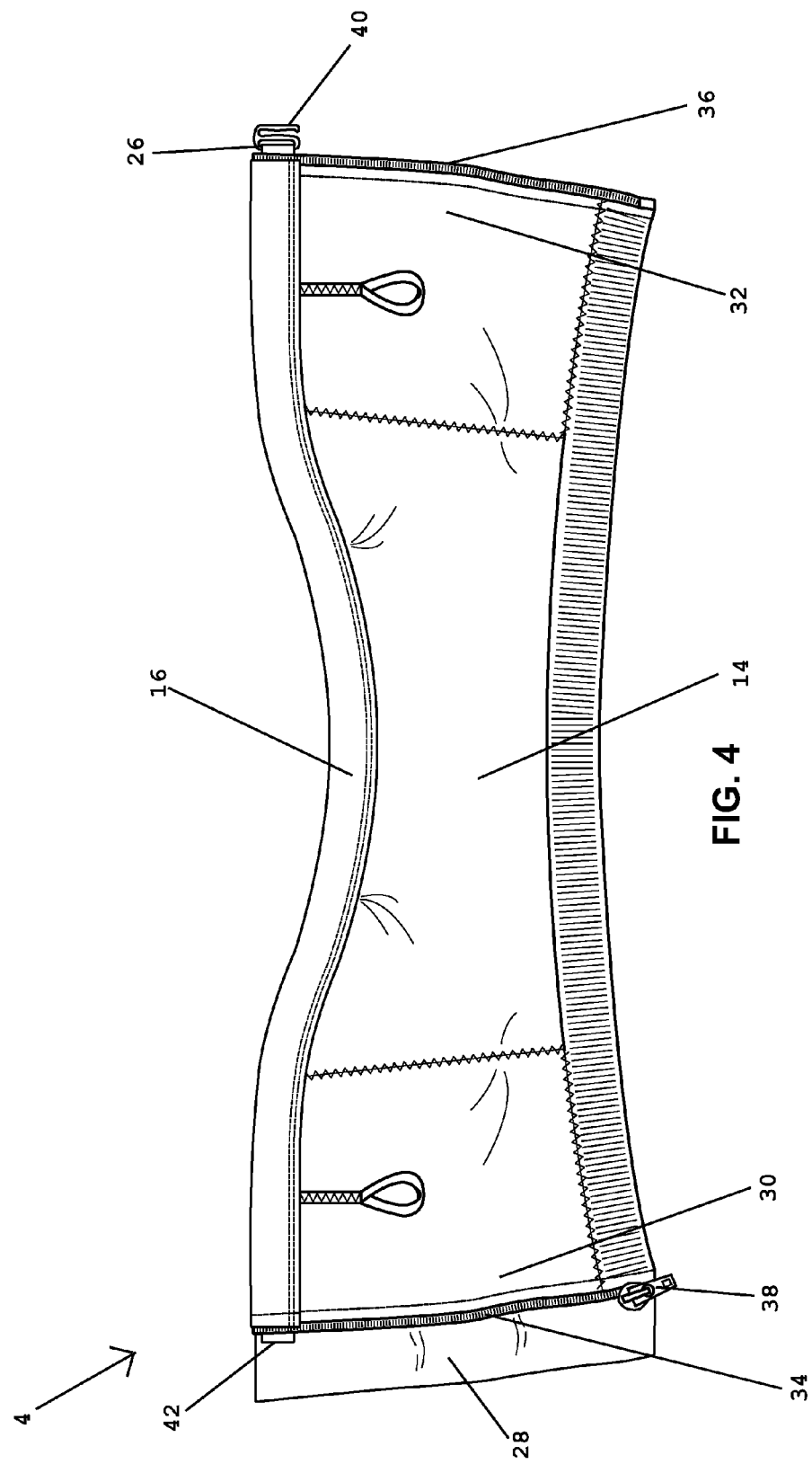
FIG. 4 is a front view of the exterior of a hands free pumping bustier in an open position.
Figure 5A:
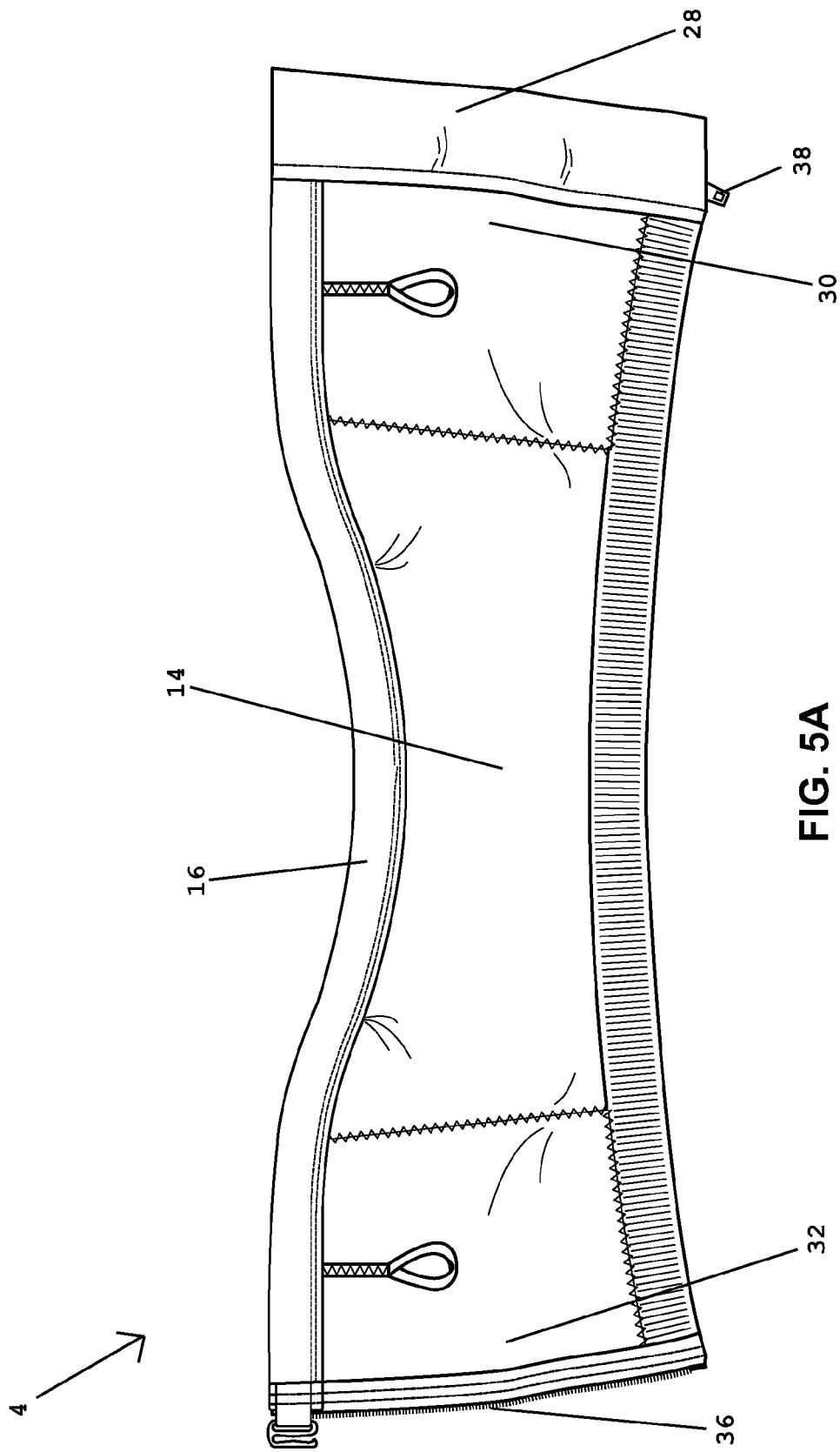
FIG. 5A is a front view of the interior of a hands free pumping bustier in an open position.

FIGS. 4 and 5A provide front exterior and front interior views, respectively, of the hands free pumping bustier 4 in an open, unzipped position. Because the hands free pumping bustier 4 is split axially to allow the wearer 2 to wrap the hands free pumping bustier 4 around the wearer's body, the hands free pumping bustier 4 has a first side 30 and a second side 32. The first side 30 has a strip of material with a first set of zipper teeth 34 and the second side 32 has a strip of material with the second set of zipper teeth 36. Either the first set of zipper teeth 34 or the second set of zipper teeth 36 has a slider 38 that is used to mate the two sets of zipper teeth 34 and 36. The protective strip of material 28 is attached to either the first side 30 or the second side 32 of the main body 14, interior of whichever set of zipper teeth 34 or 36 has the slider 38. The protective strip of material 28 is of sufficient width to protect the skin of the wearer 2 from both sets of zipper teeth 34 and 36 when the hands free pumping bustier 4 is in a closed, zipped position such as that shown in FIG. 3. In the embodiments depicted in FIGS. 4 and 5A, the first side comprises the first set of zipper teeth 34, the first set of zipper teeth has the slider 38, and the protective strip of material 28 is attached to the first side 30 of the main body 14 interior to the first set of zipper teeth 34 and slider 38.

In the embodiments depicted in FIGS. 4 and 5A, the hook 26 has a hooking portion 40 connected to the second side 32 at the top band 16, which is received in a loop portion 42 connected to the first side 30 at the top band 16. The loop portion 42 is located between the protective strip of material 28 and the strip of material with the first set of zipper teeth 34, and the hooking portion 40 is located interior to the strip of material with the second set of zipper teeth 36. The hooking portion 40 is inserted into the loop portion 42 to close the hands free pumping bustier 4 prior to zipping. The protective strip of material 28 is wide enough to protect the skin of the wearer 2 from the hooking portion 40 and the loop portion 42 when the hands free pumping bustier 4 is in a closed, zipped position such as that shown in FIG. 3.

Figure 5B:
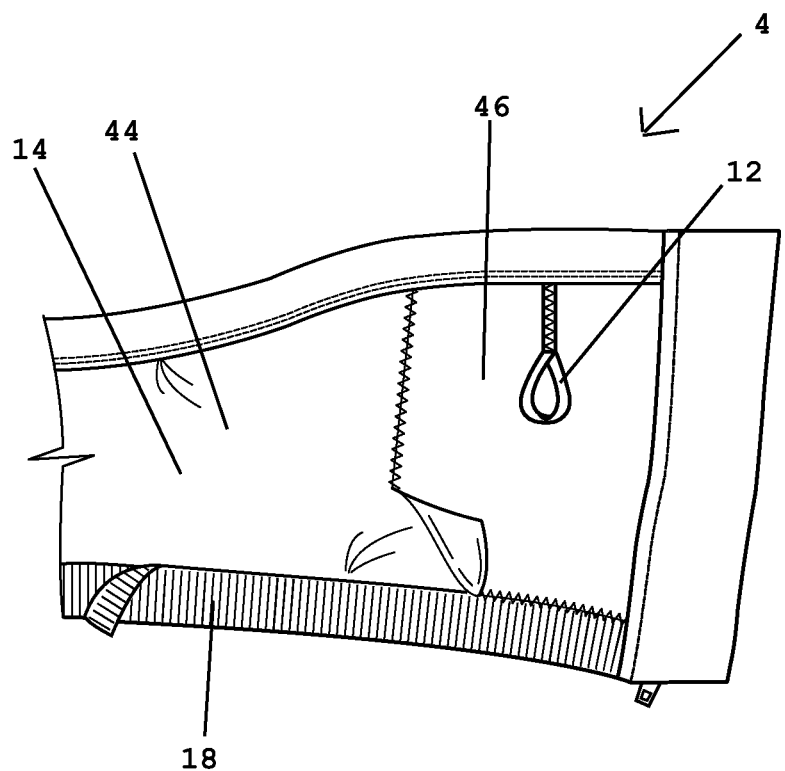
FIG. 5B is an enlarged front view of the interior of the hands free pumping bustier depicted in FIG. 5A illustrating the single-ply construction of the back of the bustier and the double-ply construction of the bottom band and portion of the bustier that covers the breast and breast shield.

FIG. 5B illustrates the number of layers of material that may be included in various portions of the hands free pumping bustier 4. As shown in FIG. 5B, the back portion 44 of the main body 14 is 1-ply thick. This single layer of material makes the hands free pumping bustier 4 lighter than it would be if the entire hands free pumping bustier 4 were 2-ply thick. However, as shown in FIG. 5A, the front portions 46 of the main body 14 surrounding the breast shield ports 12 are 2-ply thick. The double layer of material at the front portions 46 provides support around the breast shields. The bottom band 18 is also 2-ply thick, with the main body 14 preferably being folded back upon itself to form the bottom band 18. This allows the bottom band to provide additional support around the bottom of the hands free pumping bustier 4. The combination of single and doubly ply construction of the hands free pumping bustier 4 maximizes the stretch and support characteristics of the hands free pumping bustier 4.

Figure 6:
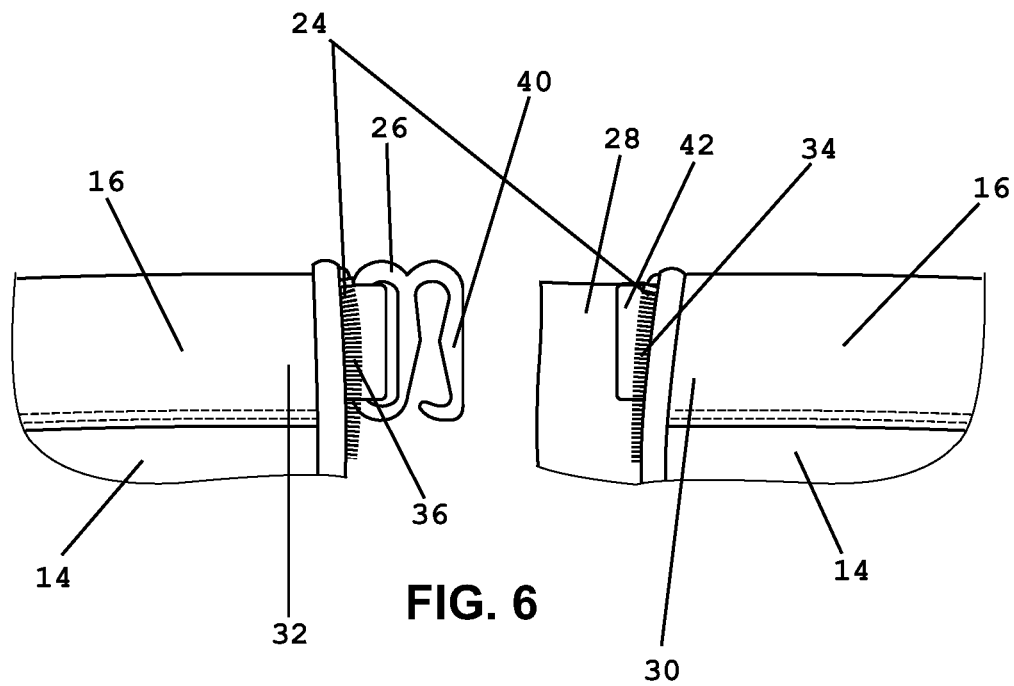
FIG. 6 is an enlarged front view of the connection between the bustier, sets of zipper teeth, hook, loop, and protective strip.
Figure 7:
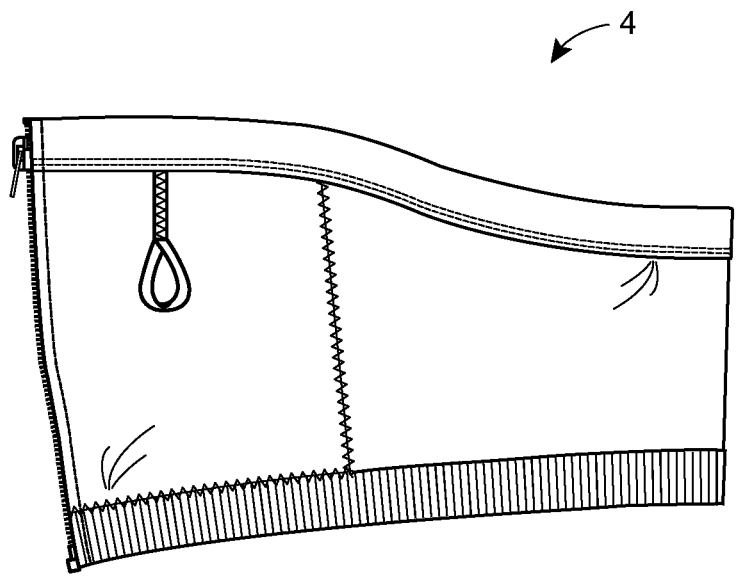
FIG. 7 is a right side view of the hands free pumping bustier in a closed position.
Figure 8:
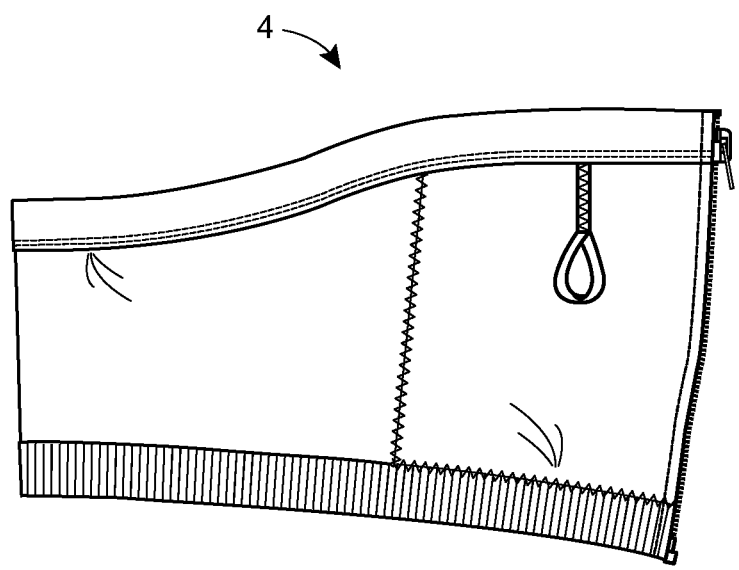
FIG. 8 is a left side view of the hands free pumping bustier in a closed position.
Figure 9:
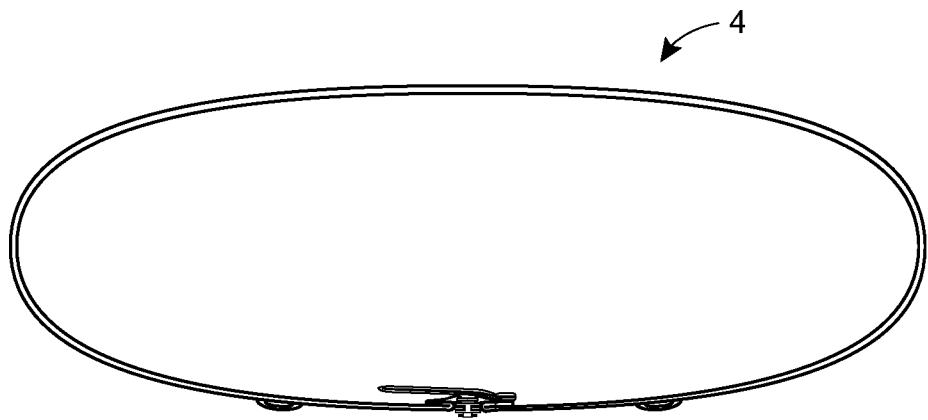
FIG. 9 is a top view of the hands free pumping bustier in a closed position.
Figure 10:
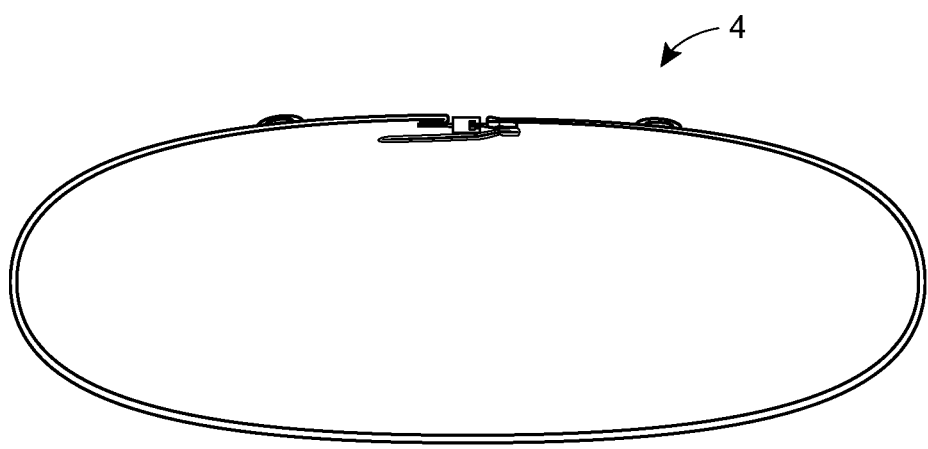
FIG. 10 is a bottom view of the hands free pumping bustier in a closed position.

FIG. 6 is an enlarged front view of the connection between the main body 14, top band 16, zipper 24, hook 26, and protective strip 28. As shown in FIG. 6, a first side 30 of the main body 14 is attached at the top band to, from interior to exterior, a protective strip 28, a loop portion 42, and a strip of material comprising the first set of zipper teeth 34 comprising the zipper slider 38 (not shown). The second side 32 of the main body 14 is attached at the top band to, from interior to exterior, a hooking portion 40 and a strip of material comprising the second set of zipper teeth 36.

In use, a wearer 2 places breast shields 8 against her breasts and then wraps the main body 14 around her body, or inserts the nipple tunnels 10 of the breast shields through the breast shield ports 12 prior to wrapping the main body 14 around her body. The wearer 2 ensures that the nipple tunnels 10 of the breast shields 8 extend through the breast shield ports 12 of the main body 14. The wearer then fastens the first side 30 of the main body 14 to the second side 34 of the main body 14 by inserting the hooking portion 40 of the hook 26 into the loop portion 42 of the hook 26. The wearer may ensure that the protective strip 28 is properly aligned underneath the hook 26 and underneath the first side 30 and second side 32 of the main body 14 prior to zipping the zipper 24. To zip the zipper 24, the wearer 2 pulls the first set of zipper teeth 34 and second set of zipper teeth 36 close to one another and pulls the slider 38 up to mate the sets of zipper teeth 34 and 36. After making any adjustments necessary to be comfortable, the wearer 2 may then attach the remainder of the breastmilk collection apparatuses 6 to the nipple tunnels 10 of the breast shields 8. Confident that the breast shields 8 are secured in place by the hands free pumping bustier 4, the wearer 2 may then proceed to pump breast milk while carrying out other tasks that may demand the use of her hands.

A suitable method for manufacturing a hands free pumping bustier 4 of the present disclosure will now be described. A circular, flat, or Warp knitting machine produces an outer ply piece of material made from a stretch nylon multi-filament yarn that is generally tubular in shape and has a first knitting pattern at a lower portion, a second knitting pattern at a higher portion, a transition line between the two knitting patterns, and a bottom band 18 knit into the outer ply piece of material. The tubular knit piece of material may, for example, be a SANTONI® knit. The tubular knit piece of material is cut or cast off around its entire circumference at the lower portion having the first knitting pattern to create a bottom and is cut or cast off around its entire circumference at the upper portion having the second knitting pattern to form a top. The tubular knit piece of material is cut or cast off in an axial direction to form a first side 30 and a second side 32. A circular, flat, or Warp knitting machine produces inner ply front portions that are sewn to the outer ply piece of material to create a main body 14 and two-ply front portions 46. Each of the breast shield ports 12 is created by cutting a slit downward from the top of the main body 14 in one of the front portions 46. The breast shield ports 12 are finished by having elastic sewn around each slit and having the upper portion of each slit sewn shut. An elastic material is sewn to the top of the main body 14 to create the top band 16. A protective liner is sewn to either the first side 30 or second side 32. A hooking portion 40 is sewn to one of the first side 30 or second side 32, and the loop portion is sewn to the other of the first side 30 or second side 32. A strip of material comprising a first set of zipper teeth 34 is sewn to the first side 30 and a strip of material comprising a second set of zipper 36 teeth mateable to the first set of zipper teeth is sewn to the second side 32.

FIGS. 7-10 depict the hands free pumping bustier 4 in a closed position from the right side, left side, top, and bottom respectively.

Figure 12:
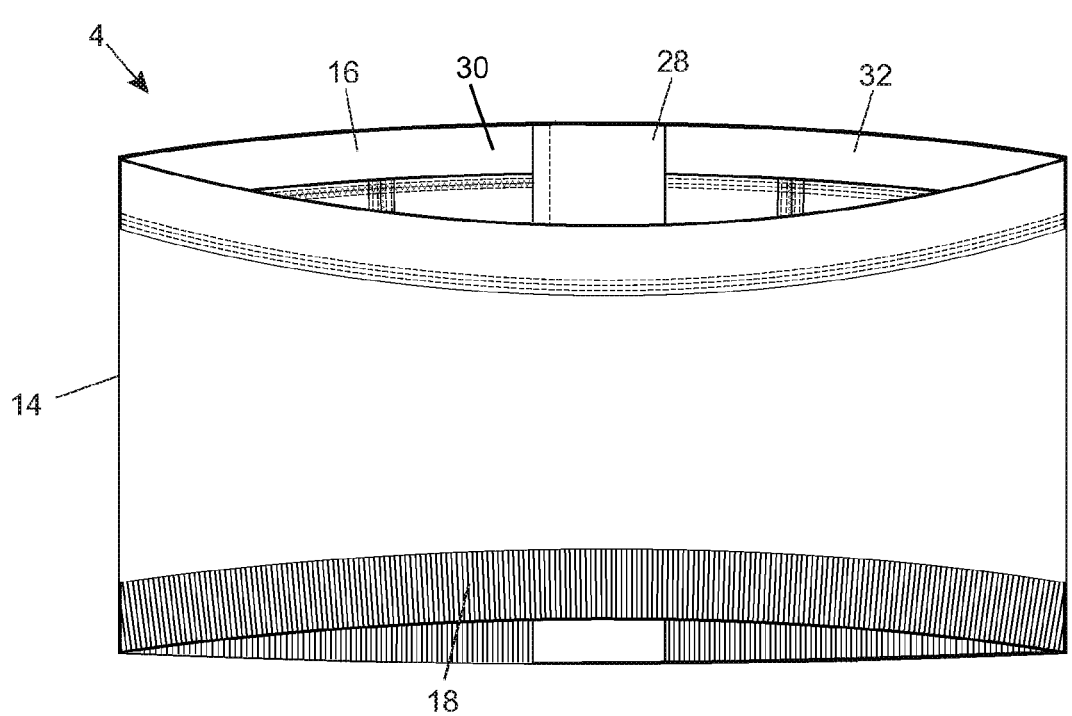
FIG. 12 is a rear view of a hands free pumping bustier in a closed position having each additional support member in a side-by-side configuration.

FIGS. 11 and 12 depict a hands free pumping bustier 4 having additional support members 20 sewn between breast shield ports 12 and top band 16 in a side-by-side configuration in which one portion of each additional support member 20 is sewn next to another portion of that same additional support member 20.

While the present disclosure has been described with respect to certain embodiments, it will be understood that variations may be made thereto that are still within the scope of the appended claims. Additionally, while a particularly-preferred embodiment is illustrated in the drawings of the present disclosure, it will be understood that the functional features disclosed and claimed herein can be accomplished in devices that differ ornamentally from these drawings, and ornamental features of the drawings are not dictated by function.

What is claimed is:

1. A bustier to facilitate hands-free breastpumping, comprising:
    a top band;
    a bottom band;
    a main body intermediate the top band and the bottom band, the main body attached at a top of the main body to the top band and formed integrally at a bottom of the main body with the bottom band, the main band having an axial split;
    a first side along the axial split;
    a second side along the axial split; and
    a pair of breast shield ports each having an additional support member, the additional support members of the breast shield ports extending superiorly of the breast shield ports to the top band.

2. The bustier of claim 1, further comprising:
    a hook connected to the top band of the bustier.

3. The bustier of claim 1, further comprising a first set of zipper teeth connected to a first side of the bustier and a second set of zipper teeth mateable to the first set of zipper teeth and connected to a second side of the bustier.

4. The bustier of claim 3, further comprising a slider located either on the first set of zipper teeth or on the second set of zipper teeth.

5. The bustier of claim 1, further comprising a protective liner on the first side or the second side.

6. The bustier of claim 1, further comprising a back portion to be worn on the back of a wearer having a single ply of material.

7. The bustier of claim 1, further comprising front portions to cover the breasts and breast shields of a wearer having two ply of material.

8. The bustier of claim 2, wherein the hook comprises a hooking portion at a top of the bustier next to the top band on one of the first side or the second side and the bustier further comprises a loop portion into which the hooking portion can be inserted at a top of the bustier next to the top band on the other of the first side or the second side.

9. The bustier of claim 1, wherein the material of the main body is made from a stretch nylon multi-filament yarn.

10. The bustier of claim 1, wherein the bottom band and main body are knit together.

11. The bustier of claim 2, wherein the top band is made from a strip of an elastic material that differs from a tubular knit piece of material used to make the main body.

12. A garment constructed to facilitate dual breast pumping comprising:
   a back portion and front portions formed of a tubular knit fabric, the front portions having increased elastic modulus as compared to the back portion and formed of multiple layers and the back portion having reduced elastic modulus as compared to the front portions and formed of a single layer;
   an integrated band formed at a bottom of the front portions and the back portion;
   a top band connected to the front portions and the back portion, the top band configured to distribute tensile forces thereacross when worn during a breast pumping session; and
   a pair of breast shield ports each having an additional support member, the additional support members of the breast shield ports extending superiorly of the breast shield ports to the top band.

13. The garment of claim 12, the top band further comprising a fastening device configured to enable distribution of tensile forces thereacross.

14. The garment of claim 12, further comprising an additional support member formed about a breast shield port, the additional support member configured to transmit force from the breast shield port to the top band by extending from the breast shield port to the top band.

15. The garment of claim 14, the additional support member comprising a continuous elastic piece sewn into the breast shield port to provide tension about a breast shield port.

16. The garment of claim 14, wherein the additional support member is sewn along slits that will become a finalized aperture in the main body thereby forming a breast shield port.

17. A method of manufacturing a bustier to facilitate hands-free breastpumping, comprising:
   using a circular, flat, or Warp knitting machine to produce an outer ply tubular knit piece of material having a first knitting pattern, a second knitting pattern, a transition line between the first and second knitting patterns, and a bottom band knit into the outer ply tubular knit piece of material along the transition line;
   cutting or casting off the tubular knit piece of material circumferentially at the first knitting pattern to create a top and circumferentially at the second knitting pattern to create a bottom and axially in one location to create a first side and a second side;
   creating inner ply front portions using a circular, flat, or Warp knitting machine;
   sewing the inner ply front portions to the outer ply tubular knit piece of material to create a main body and two-ply front portions;
   creating breast shield ports by cutting a slit downward from the top of the main body in each two-ply front portion, sewing elastic around each slit, and sewing the upper portion of each slit shut;
   stitching an elastic band to the top to make a top band.

18. The method of claim 17, and attaching a protective liner on the first side or the second side.

19. The method of claim 17, and attaching a first set of zipper teeth to the first side and a second set of zipper teeth that is mateable to the first set of zipper teeth to the second side.

20. The method of claim 17, and attaching a hook portion next to the top band on the first side or the second side and attaching a loop next to the top band on the other of the first side or the second side.

* * * * *